United States Patent
Yadav et al.

(10) Patent No.: US 7,056,540 B2
(45) Date of Patent: Jun. 6, 2006

(54) **ENZYMATIC PROCESS FOR THE PREPARATION OF OPTICALLY ACTIVE ALCOHOLS FROM KETONES USING TUBEROUS ROOT *DAUCUS CAROTA***

(75) Inventors: Jhillu Singh Yadav, Hyderabad (IN); Samik Nanda, Hyderabad (IN); Polepally Thirupathi Reddy, Hyderabad (IN); Adari Bhaskar Rao, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 509 days.

(21) Appl. No.: 10/282,066

(22) Filed: Oct. 29, 2002

(65) Prior Publication Data

US 2004/0082043 A1   Apr. 29, 2004

(51) Int. Cl.
*A01N 65/00*   (2006.01)

(52) U.S. Cl. ............... 424/773; 424/725; 435/125; 435/128; 435/130; 435/131; 435/135; 435/148; 435/155; 435/156; 435/157

(58) Field of Classification Search ........... 424/725, 424/728, 773, 125; 435/128, 130, 131, 135, 435/148, 155, 156, 157, 125
See application file for complete search history.

(56) References Cited

U.S. PATENT DOCUMENTS

2001/0044142 A1* 11/2001 Brown et al. ............ 435/156

\* cited by examiner

*Primary Examiner*—Herbert J. Lilling
(74) *Attorney, Agent, or Firm*—Birch,Stewart,Kolasch & Birch,LLP

(57) ABSTRACT

The present invention relates to an enzymatic process for the preparation of optically active chiral alcohols using tuberous root *Daucus carota*; particularly invention relates to an enzymatic process for the preparation of optically active alcohols by enantioselective reduction of corresponding ketones using tuberous root *Daucus carota*.

12 Claims, 3 Drawing Sheets

Figure 1:
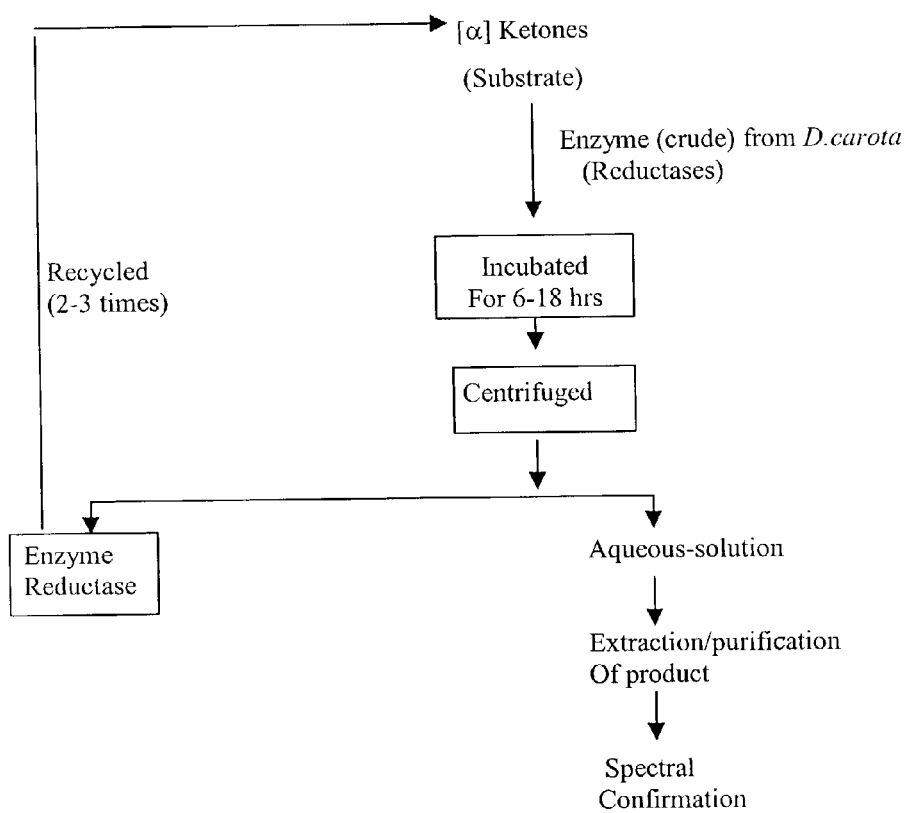

Figure 1: Flow sheet of a novel enzymatic process for enantioselective reduction of ketones using tuberous root *Daucus carota*.

Figure 2:
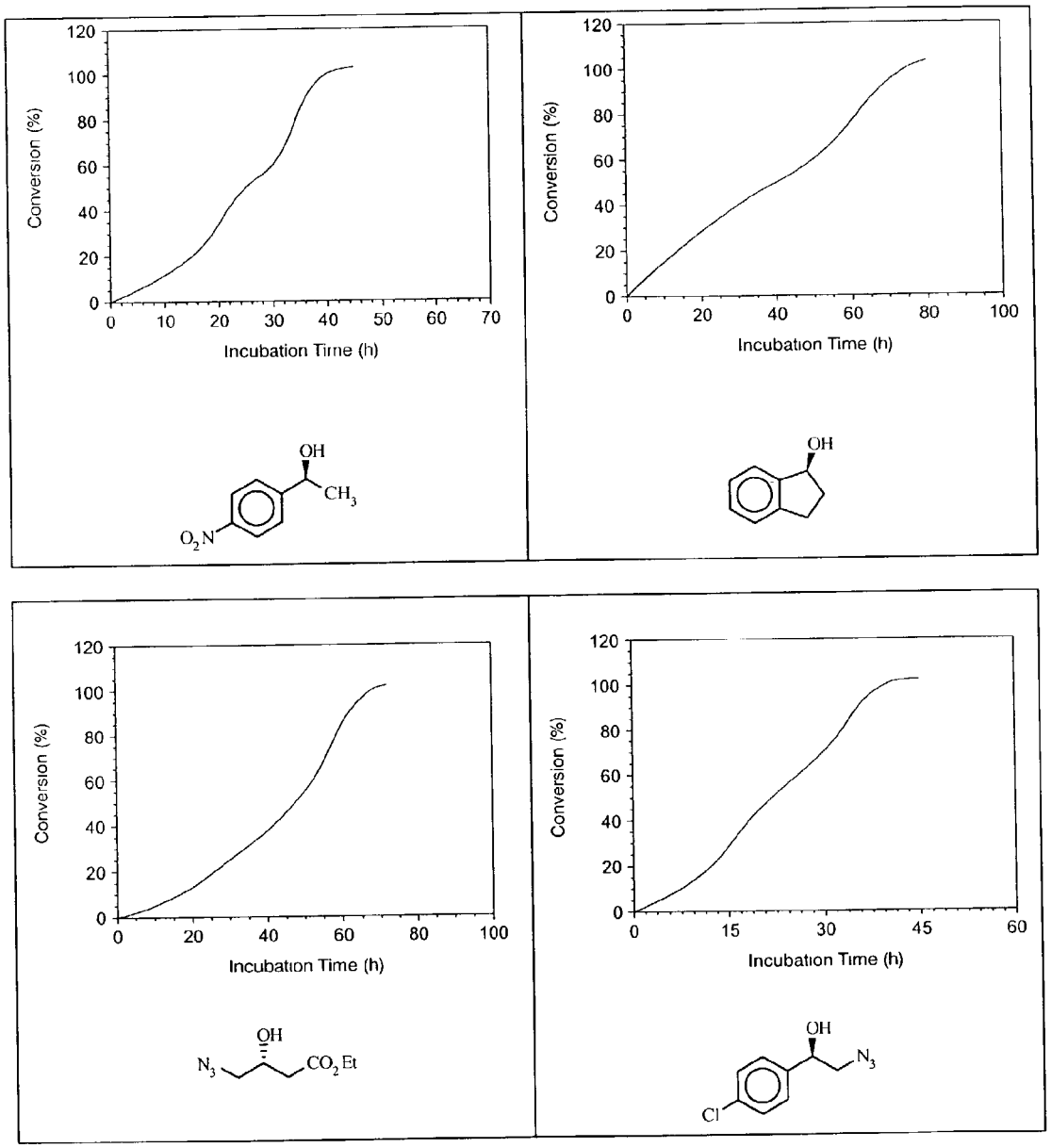

Fig. 2: Conversion chart for some of the ketones with *Daucus carota* root.
Standard conversion charts were given for all class of compounds (Fig.2).

Figure 2A:
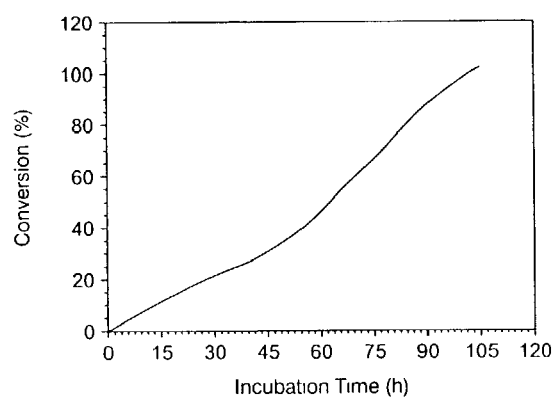
Figure 2A:
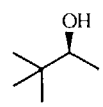

Fig. 2a: Conversion chart for some of the ketones with *Daucus carota* root

ENZYMATIC PROCESS FOR THE PREPARATION OF OPTICALLY ACTIVE ALCOHOLS FROM KETONES USING TUBEROUS ROOT *DAUCUS CAROTA*

FIELD OF THE INVENTION

This invention relates to an enzymatic process for the preparation of optically active chiral alcohols using tuberous root Dallcus *carota*. More particularly, the present invention relates to an enzymatic process for the preparation of optically active alcohols by enantioselective reduction of corresponding ketones using tuberous root *Daucus carota*.

BACKGROUND AND PRIOR ART REFERENCES

In recent years, great attention has been paid to asymmetric synthesis of chiral synthons that are used in developing modern drugs and agrochemicals. Chiral alcohols are one of the well-known synthons that can be obtained from corresponding prochiral ketones by asymmetric reduction.

However, numerous reduction reactions were carried out using different chemical and biocatalyst reductions (Corey. E. J., Helal, G. J. Angewantha Chern Int. Eng. (1998) 91 (1986) and Csuk, R. et al. Chern. Rev. (1991) 91 46; these reactions have some difficulties in attaining high chemical yield and optical purity under ecofriendly conditions. Asymmetric reduction by means of chemical methods involves use of expensive chiral reagents and environmental hazardous heavy metals. On the contrary use of biocatalyst microorganisms or plant cells for reduction of prochiral ketones yielding the corresponding optically active alcohols with excellent enantioselectivity are of present day interest.

The applicants now for the first time describe the novel methodology in oxido reduction of some of the pro-chiral functional keto functionalities e.g., acetophenones, cyclic ketones, β-keto esters, azidoketones and aliphatic ketones etc. along with their corresponding substituents using crude reductive enzymes isolated from tuberous roots carrot (D.corta) with yields ranging from 70–98%, with Ees' 92–98%, most preferably showing 'S' configurations. The final reduction products in all the cases leading to valuable chiral intermediates, which can be further used for total synthesis of various drugs and agrochemicals.

OBJECTS OF THE INVENTION

The main object of the present invention is to provide a process for the preparation of optically active chiral alcohol from corresponding ketones using a crude extract of *Daucus carota* or an enzyme reductase isolated from *Daucus carota*.

Another object of the invention is to provide a process of reducing optically active chiral ketones using a crude extract of *Daucus carota* or an enzyme reductase isolated from *Daucus carota* to produce corresponding optically active chiralalcohols.

SUMMARY OF THE INVENTION

Accordingly, the present invention provides an enzymatic process for the preparation of optically active chiral alcohols using tuberous root *Daucus carota*. More particularly, the present invention relates to an enzymatic process for the preparation of optically active alcohols by enantioselective reduction of corresponding ketones using tuberous root *Daucus carota*.

This invention involves the enantioselective reduction of ketones using a reducing enzyme (reductase) isolated from tuberous roots for example carrot and beet root. Stereochemistry is one of the most important parameters governing the biological activity of organic compounds. Therefore, chirality is emerging as a key for both academic and industrial laboratories in synthesis of organic chemicals in the area of pharmaceuticals and agrochemicals. Benefits from the use of single enantiomers include avoidance of gratuitous environmental contamination, separation of interfering activity or toxicity and less material to be processed with reduced cost and effluent treatment.

DETAILED DESCRIPTION OF THE INVENTION

Accordingly, the present invention provides a process for the preparation of optically active chiral alcohols from ketones, said process comprising reducing the ketones to corresponding optically active chiral alcohols using a crude extract of *Daucus carota* or an enzyme reductase isolated from *Daucus carota*

One embodiment of the invention provides a process comprising adding a ketone to a crude extract of *Daucus carota* in about 0.1 M to 2.0 M buffer of pH ranging between 6.0 to 8.0, incubating the reaction mixture at a temperature of 25 to 40° C. for a period ranging from 10 to 110 hours, and isolating the product followed by purification to obtain the desired product.

In another embodiment of the invention, the incubation is preferably carried out at a temperature in the range of 35 to 40° C.

In another embodiment of the invention, the ketone used is selected from a group consisting of unsubstituted/substituted ketones, from alkyl aryl ketones, cyclic ketones, β-ketoesters, azido ketones and aliphatic ketones.

In still another embodiment, the alkylaryl ketone is selected from the group consisting of p-chloro acetophenone, p-bromo acetophenone, p-fluoro acetophenone, p-nitro acetophenone, p-methyl acetophenone, p-methoxy acetophenone, p-hydroxy acetophenone, 1-(2-naphthyl)-1-ethanone, 1-(6-methyl-2-naphthyl)-1-ethanone and 1-(2-furyl)-1-ethanone.

In still another embodiment, the cyclic ketone is selected from a group consisting of -tetralone, 2-tetralone, 6-methoxy-1-tetralone and 1-indalone.

In yet another embodiment, the p-ketoester is selected from a group consisting of ethylacetoacetate, ethyl-4-chloro-3-oxobutanoate, ethyl-4-bromo-3-oxobutanoate, ethyl-4-azido-3-oxobutanoate, ethyl-3-oxo-3-phenylpropanoate, ethyl-4,4,4 trichloro-3-oxobutanoate, 4,4,4 trifluoro-3-oxobutanoate, ethyl-3-oxo-4-phenylsulfonylbutanoate, ethyl-2-oxo-1-cyclopentanecarboxylate and ethyl-2-oxo-1-cyclohexanecarboxylate.

In yet another embodiment, the substituted azidoketone is selected from a group consisting 2-azido-1-phenyl-1-ethanone, 2-azido-1-(4-chlorophenyl)-1-ethanone, 2-Azido-1-(4-methylphenyl)-1-ethanone, 2-azido-1-(4-methoxlphenyl)-1-ethanone, 2-azido-1-(4-fluorophenyl)-1-ethanone, 2-azido-1-(4-fluorophenyl)-1-ethanone, 2-azido-(4-tertbutyldimethyl-silyloxyphenyl)-1-ethanone, 2-azido-1-(2-furyl)-1-ethanone, 2-azido-1-(2-thienyl)-1-ethanone and 2-azido-1-(2-napthyl)-1-ethanone.

In still another embodiment, the substituted open chain ketone is selected from a group consisting 2-butanone, 2-pentanone, 2-hexanone, 4-methyl-2-pentanone, 3,3-dimethyl-2-butanone and 2-heptanone.

In yet another embodiment, the substituted ketone is selected from a group consisting acetophenone, tetralone, ethylacetoacetate, 2-azido-1-phenyl-1-ethanone and 2-hexanone.

Another embodiment of the present invention provides a process, wherein the buffer used is selected from sodium phosphate, sodium acetate, potassium phosphate, potassium acetate, and tris HCl.

In another embodiment, the incubation period used is preferably in the range of 30 to 100 hours.

In another embodiment, the reductase enzyme after completion of the reduction is filtered, washed with a buffer solution and again used for carrying out a reduction reaction.

In another embodiment, the percentage yield of optically active chiral alcohol consisting of aliphatic and aromatic alcohol obtained from the corresponding ketone is in the range of 30–95 wt percent;

Yet another embodiment, the optical purity (ee) of chiral alcohols obtained is in the range of 90 to 100%.

BRIEF DESCRIPTION OF THE ACCOMPANYING DRAWING

FIG. 1: Flowsheet of a novel enzymatic process for enantioselective reductions of ketones using tuberous root *Daucus carota*.

FIGS. 2 & 2a represent conversion charts for some of the ketones obtained using *Daucus carota* root.

DETAILED DESCRIPTION OF THE INVENTION

Reduction of ketones with *Daucus carota* root: Ketones (50–200 mg) were added to a stirred suspension of freshly cut/homogenized tuberous root *Daucus carota* (5–25 gm, protein content 9–15 gm/ml Biuret method) in 50–100 ml of 0.1 to 2 M sodium phosphate buffer pH 6 to 8 and the reaction mixtures containing substrate (100–500 mg) were stirred at temperatures 25 to 35° C. for the incubation time of 10 to 20 hrs to obtain the appropriate conversion. Filtrates containing products were extracted in polar organic solvents. The organic phase was dried in anhydrous $Na_2SO_4$ and then concentrated in vacuum. The final products were purified by flash chromatography and the compound structure was confirmed by spectral data.

For the mini preparative scale reactions, the substrate ketones (5–10 gm) were taken in a conical 2 L flask and water (500–800 ml) was added to it followed by addition of freshly cut/isolated reductase from carrot (100–500 g). The reaction mixture was stirred in an incubator shaker for the required time (10–90 hrs), later the product alcohol was extracted and the structures were confirmed by known spectral data.

Preparative scale production: Several ketones that afforded high enantioselectivity for the reduction on a small scale were taken up for a large batch (30–50 gm) synthesis of chiral alcohols. The isolated yields and Ees of the reduction were summarized in Table 6.

The applicants have also performed the reduction of some ketones with *Daucus carota* root in an aqueous-organic biphasic reaction system. Common organic solvents, which were immiscible in water, have been used e.g., ethylacetate, hexane, cyclohexane, etc. However, the rate of reaction decreased significantly, due to enzyme unstability in organic solvents.

Recycling of the *Daucus Carota* root: After reaching the completion of the reduction reaction the mixture was filtered and the crude enzyme of *D. carota* washed successively with buffer pH 7.4. The crude enzyme was again reused to carry out a reduction reaction. It was observed that the activity of the enzymes was decreased significantly; only 20–30% conversion was achieved for acetophenone, after four repeated experiments.

The following examples are given by the way of illustration and should not be construed to limit the scope of the invention.

EXAMPLE 1

Reduction of Acetophenones

Acetophenone and substituted acetophenones undergoes the reduction in a well-defined fashion (Scheme 1). Several substituted acetophenones have been studied, a few examples are depicted in Table 1. For almost all compounds the reduction was completed within 2–3 days. Excellent chemical yields (70–80%) and optical purity<90%) were observed. The substituted product aryl alcohol having (S) configuration was obtained, which was in perfect agreement with Prelog's rule. It was observed that presence of electron-donating substituents in the aromatic ring (-Me, -Ome) decreased the rate of reaction. No influence on the steric course of the reduction was observed.

Scheme 1: Reduction of acetophenones

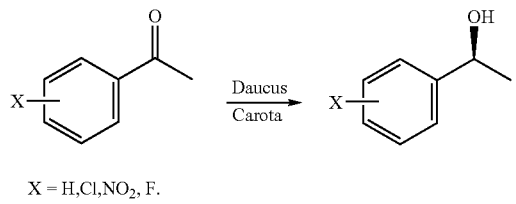

$X = H, Cl, NO_2, F.$

The General Methodology for the Reduction of the Substituted Acetophenones:

100 mg of each of the compounds in Table 1 entry No. 1–10 and other similarly related compounds were added to a crude extract of 2 gm *Daucas carota* (protein 1 gm/ml) in 50 ml of 0.1 M sodium phosphate buffer pH 6.5 to 7.5. The reactions were incubated in a shaking incubator for 30 to 50 hours. The product formed was isolated and purified by flash chromatography and the product obtained was confirmed by standard spectral data.

Selected Spectral Data of Representative Product:

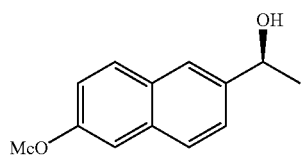

$^1$H: 7.8 (m, 4H), 7.45 (m, 3H), 5.0 (m, 1H), 1.8 (d, J=6 Hz, 3H). $[\alpha]_D^{25}=-31.0$ (c=1.5, $CHCl_3$). Elemental analysis: Calculated C, (77.20%); H, (6.98%); Found C, (77.15%); H, (7.00%).

EXAMPLE 2

Reduction of Cyclic Alkanones

Different substituted tetralones and indanone were reduced efficiently with *Daucus carota* root (Scheme 2) and the reaction was completed within 3 days (Table 2) as determined by GC. The enantioselectivity was <95% as determined by chiral HPLC. The absolute configuration of the product alcohol (substituted tetralone alcohols) observed was (S), as predicted by Prelog's rule.

Scheme 2: Reduction of cyclic ketones

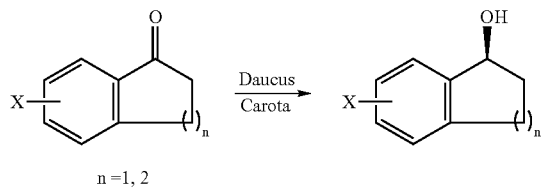

n = 1, 2

The General Methodology for the Reduction of Substituted Cyclic Ketones:

100 mg of each of the compounds in Table 2, the entry Nos. 1–3 and their related substituted a cyclic ketone were added to separate flasks (100 ml) containing crude homogenized extract of *Daucus carota* (2 gm), protein 19 mml, suspended in 50 ml 0.1 M sodium phosphate buffer pH 6.5. The reaction was incubated in a shaking incubator for 40 to 80 hours respectively. The product formed was isolated and purified by column chromatography, the structure of the compound was confirmed by spectral data.

Selected Spectral Data of Representative Product:

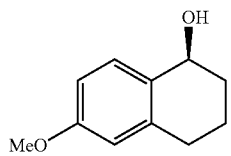

$^1$H: 7.15 (m, 1H), 7.0 (m, 1H), 6.8 (m, 1H), 4.7 (m, 1H), 3.8 (s, 3H), 2.7 (m, 1H), 2.5 (m, 1H), 2.0 (m''' 4H). $[\alpha]D^{25}=+10.1$ (c=1.75, CHCl$_3$). Elemental analysis: Calculated C, (74.13%); H, (7.92%); Found C, (74.16%); H, (7.88%).

EXAMPLE 3

Reduction of β-Ketoesters

Reduction of β-keto esters were probably the most extensively studied in particular reference to small molecules, using microbial transformations leading to chiral intermediates in asymmetric synthesis. Recently some discrepancies regarding the Ee and chemical yield have been reported when using Baker's yeast-mediated reduction of β-ketoesters, whereas using the enzyme isolated from *Daucus Carota* root as a biocatalyst, the reduction of substituted β-keto ester compound gave the products substituted β-hydroxy esters in high chemical yield and optical purity within 3–4 days. (Table 3). Higher enantioselectivity of the cyclic β-ketoesters was observed compared to that of open chain β-ketoesters.

The general stereochemical feature of the reaction in most cases is well explained by Prelog's rule. However, it was established that the absolute configuration and the optical purity of the products depend strongly both upon the nature and the size of the substituents adjacent to the carbonyl group and of the ester moiety. For compounds 4, 7 and 8 the opposite stereochemistry was observed as predicted from Prelog's rule.

Scheme 3: Reduction of β – ketoesters

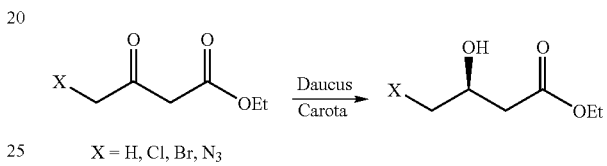

X = H, Cl, Br, N$_3$

The General Methodology for the Reduction of Substituted β-Ketoesters:

100 mg of each of the compounds in Table 3, entry Nos. 1–10 and their related substituted β-ketoesters were added to a 100 ml flask containing 2 gm of crude extract of *Daucus carota*, and 50 ml of 0.1 M sodium phosphate buffer pH 6.0 to 7.5 were added. The reaction was incubated in a shaker for 50 to 70 hours for maximum product formation. The product formed was isolated, purified by column chromatography and the structure of the compound was confirmed by spectral data.

Selected Spectral Data of Representative Product:

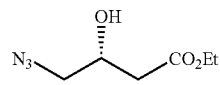

$^1$H: 4.2 (q, J=7 Hz, 2H), 4.1 (m, 1H), 3.3 (m, 2H), 3.15 (brs, —OH), 2.5 (m, 2H), 1.25 (t, J=7 Hz, 3H). $[\alpha]D^{25}=+7.2$ (c=3.1, CHCl$_3$)). Elemental analysis: Calculated C, (41.14%); H, (7.48%); and N, (23.99%); Found C, (41.20%); H, (7.52%); N, (23.92%).

EXAMPLE 4

Reduction of Azidoketones

Synthesis of chiral azido alcohols, which are used in the total synthesis of various drugs, was studied by reduction of different substituted azodiketones with *Daucus Carota* root (Scheme 4). The reaction was usually completed within 2–3 days (Table 4). Both the chemical yield and the optical purity of the product azido alcohols were excellent. No influence on the steric course of the reduction was observed due to electron-donating substituents.

Scheme 4: Reduction of azidoketones

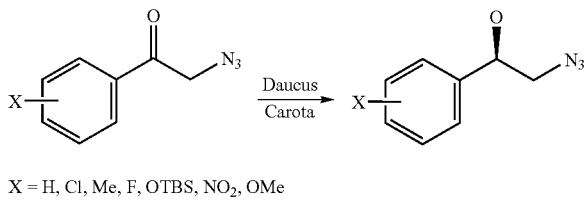

X = H, Cl, Me, F, OTBS, NO₂, OMe

The General Methodology for Reduction of Substituted Azido Ketones:

100 mg of each of the compounds in Table 4, entry Nos. 1 to 10 and their related substituted azido ketones were added to a flask (100 ml) containing the extract of *Daucus carota* (2 gm), and 50 ml of 0.1M sodium phosphate buffer pH 7.0 to 7.5 were added. The reaction was carried out for period of 40 to 80 hours for product formation. The product formed was isolated, purified and the structure was confirmed by spectral data.

Selected Spectral Data of Representative Product

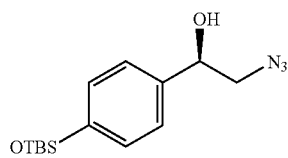

$^{1}$H, 7.25 (d, J=7.2 Hz, 2H), 6.85 (d, J=7.2 Hz, 2H), 4.8 (m, 2H), 2.35 (brs, 1H), 1.0 (s, 9H), 0.2 (s, 6H). $^{13}$C: −4.46, 25.62, 58.1, 73.09, 120.24, 127.0, −127.1, 133.1. $[\alpha]D^{25}=-59.2$ (c=1.0, CHCl$_3$).

Elemental analysis: Calculated C, (57.11%); H, (8.22%); N, (14.27%); Found C, (57.14%); H, (8.24%); N, (14.22%).

EXAMPLE 5

Reduction of Aliphatic Ketones

It is difficult to obtain pure simple aliphatic secondary alcohols by the reduction of corresponding ketones with chemical methods in spite of their importance in building chiral blocks. In our case open chain aliphatic ketones can be reduced with *Daucus Carota* root as a biocatalyst. The yields of the products were lower when compared to the other alcohols, as the product alcohols were easily evaporated during the process of purification due to their low boiling point. The absolute configuration of the product alcohol was (S), which means the addition of hydride ion follows Prelog's rule. Among the five and other related classes of ketones it was observed that acetophenone and some of the azidoketones need less reaction time, e.g. 10–20 hrs., whereas all other ketones need longer reaction time.

The General Methodology for Reduction of Substituted Aliphatic Ketones:

100 mg of each of the compounds in Table 5, entry Nos. 1 to 6 and their related substituted aliphatic ketones were taken into a conical flask (100 ml) containing crude extract of *Daucus Carota*, and 50 ml of 0.1M sodium phosphate buffer pH 6.5 to pH 7.5 were added. The reaction was incubated for 80 to 100 hours for maximum conversion. The product isolated was purified by column chromatography and the structure of the compound was confirmed by spectral data.

Selected Spectral Data of Representative Product:

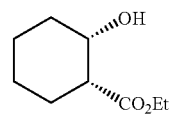

$^{1}$H: 4.18 (q, J=7 Hz, 2H), 4.13 (m, 1H), 3.1 (brs, —OH), 2.4 (ddd, J=2.5, 4.0 & 11 Hz, 1H), 2.0 (m, 2H), 1.9 (m, 2H), 1.1 (m, 7H), 13C: 175.8, 67, 47, 31, 25, 23, 23.5, 20.2, 15. $[\alpha]D^{25}=+28.9$ (c=2.0, CHCl$_3$). Elemental analysis: Calculated C, (62.40%); H, (9.89%); Found C, (62.35%); H, (9.90%).

TABLE 1

Reduction of substituted acetophenones with *Daucas Carota* root.

| Entry | Compound | pH | Time of Conversion (h) | Yield (%)[a] | Ee (%)[b] | Configuration |
|---|---|---|---|---|---|---|
| 1 | Acetophenone | 7.5 | 40 | 73 | 92 | S |
| 2 | p-chloro acetophenone | 6.5 | 42 | 76 | 95 | S |
| 3 | p-bromo acetophenone | 7.0 | 48 | 61 | 95 | S |
| 4 | p-fluro acetophenone | 7.0 | 41 | 80 | 90 | S |
| 5 | p-nitro acetophenone | 7.0 | 40 | 82 | 96 | S |
| 6 | p-methyl acetophenone | 6.5 | 50 | 75 | 92 | S |
| 7 | p-methoxy acetophenone | 6.5 | 45 | 72 | 94 | S |
| 8 | P-hydroxy acetophenone | 7.0 | 47 | 73 | 91 | S |
| 9 | 1-(2-napthyl)-1-ethanone | 7.0 | 49 | 70 | 97 | S |
| 10 | 1-(6-methoxy-2-napthyl)-1-ethanone | 7.0 | 42 | 78 | 98 | S |
| 11 | 1-(2-furyl)-1-ethanone | 7.0 | 50 | 65 | 92 | S |

[a]All the compounds incubated at 37–40° C., isolated yields after chromatographic separation

[b]determined from chiral HPLC as well as comparing the rotation with the literature value.

TABLE 2

Reduction of substituted cyclic ketones with *Daucus carota* root

| Entry | Compound | pH | Time of Conversion (h) | Yield (%)[a] | Ee (%)[b] | Configuration |
|---|---|---|---|---|---|---|
| 1 | 1-Tetralone | 6.5 | 70 | 52 | 96 | S |
| 2 | 2-Tetralone | 6.5 | 72 | 58 | 95 | S |
| 3 | 6-Methoxy-1-tetralone | 6.5 | 69 | 60 | 93 | S |
| 4 | 1-Indalone | 6.5 | 78 | 57 | 98 | S |

All the compounds incubated at 37–40° C.

TABLE 3

Reduction of substituted β-ketoesters with *Daucus Carota* root

| Entry | Compound | pH | Time of conv.(h) | Yield (%)$^a$ | Ee (%)$^b$ | Configuration |
|---|---|---|---|---|---|---|
| 1 | Ethylacetoacetate | 6.0 | 58 | 58 | 95 | S |
| 2 | Ethyl-4-chloro-3-oxobutanoate | 7.0 | 60 | 50 | 90 | S |
| 3 | Ethyl-4-bromo-3-oxobutanoate | 7.0 | 62 | 53 | 95 | S |
| 4 | Ethyl-4-azido-3-oxobutanoate | 7.0 | 65 | 68 | 90 | R |
| 5 | Ethyl-3-oxo-3-phenylpropanoate | 7.0 | 56 | 62 | 98 | S |
| 6 | Ethyl-4,4,4 trichloro-3-oxobutanoate | 6.5 | 70 | 51 | 88 | S |
| 7 | Ethyl-4,4,4 trifluoro-3-oxobutanoate | 6.5 | 56 | 72 | 78 | R |
| 8 | Ethyl-3-oxo-4-phenylsulfonylbutanoate | 7.5 | 66 | 70 | 98 | R |
| 9 | Ethyl-2-oxo-1-cyclopentanecarboxylate | 7.5 | 60 | 60 | 97 | IR, 2S |
| 10 | Ethyl-2-oxo-1-cyclohexanecarboxylate | 7.5 | 62 | 63 | 98 | IR, 2S |

All the reactions are incubated at 37–40° C.

TABLE 4

Reduction of substituted azidoketones with *Daucus carota* root

| Entry | Compound | pH | Time of conv.(h) | Yield (%)$^a$ | Ee (%)$^b$ | Configuration |
|---|---|---|---|---|---|---|
| 1 | 2-Azido-1-phenyl-1-ethanone | 7.0 | 42 | 70 | 100 | R |
| 2 | 2-Azido-1-(4-chlorophenyl)-1-ethanone | 7.2 | 40 | 72 | 98 | R |
| 3 | 2-Azido-1-(4-chlorophenyl)-1-ethanone | 7.0 | 58 | 71 | 98 | R |
| 4 | 2-Azico-1-(4-chlorophenyl)-1-ethanone | 7.0 | 78 | 58 | 99 | R |
| 5 | 2-Azido-1-(4-chlorophenyl)-1-ethanone | 7.5 | 60 | 65 | 95 | R |
| 6 | 2-Azido-1-(4-chlorophenyl)-1-ethanone | 7.0 | 66 | 77 | 97 | R |
| 7 | 2-Azido-(4-tertbutyldimethyl-silyloxyphenyl)-1-ethanone | 7.5 | 78 | 62 | 96 | R |
| 8 | 2-Azido-1-(2-furyl)101ethanone | 7.0 | 52 | 69 | 92 | S |
| 9 | 2-Azido-1-(2-furyl)101ethanone | 7.0 | 69 | 58 | 94 | S |
| 10 | 2-Azido-1-(2-furyl)101ethanone | 7.0 | 70 | 49 | 93 | R |

All the reactions are incubated at 37–40° C.

TABLE 5

Reduction of substituted open chain ketones with *Daucus Carota* root

| Entry | Compound | pH | Time of Conversion (h) | Yield (%)$^a$ | Ee (%)$^b$ | Configuration |
|---|---|---|---|---|---|---|
| 1 | 2-butanone | 7.0 | 80 | 38 | 87 | S |
| 2 | 2-pentanone | 7.5 | 88 | 49 | 82 | S |
| 3 | 2-hexanone | 7.0 | 85 | 50 | 90 | S |
| 4 | 4-methyl-2-pentanone | 7.5 | 90 | 32 | 71 | S |
| 5 | 3,3-dimethyl-2-butanone | 7.5 | 102 | 49 | 75 | S |
| 6 | 2-heptanone | 7.0 | 86 | 30 | 92 | S |

All the reactions are carried out 35–40° C.

TABLE 6

Reduction of substituted ketones on a preparative scale

| Substrate | Substrate/Carrot (w/w) gm | Isolated yield (%) | Ee (%) | Configuration |
|---|---|---|---|---|
| Acetophenone | 1/10 | 75 | 90 | S |
| Tetralone | 1/10 | 68 | 95 | S |
| Ethylacetoacetate | 1/10 | 65 | 92 | S |
| 2-azido-1-phenyl-1-ethanone | 1/10 | 40 | 94 | R |
| 2-hexanone | 1/10 | 25 | 90 | S |

All the reactions are carried out at 35–40° C. at pH 7.0.

TABLE 7

Reduction of substituted ketones on a preparative scale

| Substrate | Substrate/Yeast (w/w) | Isolated yield (%) | Ee (%) | Configuration |
|---|---|---|---|---|
| Acetophenone | ½ | 40 | 60 | S |
| Tetralone | ½ | 35 | 55 | S |
| Ethylacetoacetate | ½ | 26 | 35 | S |
| 2-azido-1-phenyl-1-ethanone | ½ | 35 | 50 | R |
| 2-hexanone | ½ | 38 | 45 | S |

Incubation time and temperature depend upon the substrate and source of the enzymes used.

Advantages:

Advantages of a novel enzymatic process using tuberous root *Daucus carota* in catalyzing the enantioselective reduction of ketones.

1. The reaction conditions employed to develop chiral alcohols from corresponding ketones are simple, economical and eco-friendly conditions with high enantioselectivity and yields.
2. The advantages to this reduction over the traditional yeast mediated reduction are:
    a) Easy availability
    b) Low cost of the enzyme source
    c) Easy isolation/separation of the product from the reaction medium, useful in scale-up process

The invention claimed is:

1. A process for the preparation of an optically active chiral alcohol by reducing the corresponding ketone using a homogenate of root of *Daucus carota*, the process comprising steps of
   a.) adding the ketone to the homogenate of root of *Daucus carota* in the presence of 0.1 M to 2.0 M buffer solution having a pH ranging between 6.0 to 8.0,
   b.) incubating the reaction mixture of step (a) at a temperature range of 25° C. to 40° C. for a time period ranging from 10 to 110 hours,
   c.) isolating a crude product containing optically active chiral alcohol from the reaction mixture; and
   d.) purifying the crude product to obtain pure optically active chiral alcohol.

2. The process as claimed in claim 1, wherein the incubation step b) is carried out at a temperature in the range of 35 to 40° C.

3. The process as claimed in claim 1, wherein the ketone used is selected from a group consisting of alkylaryl ketones, cyclic ketones, β-ketoesters, azido ketones and aliphatic ketones.

4. The process as claimed in claim 3, wherein an alkylaryl ketone selected from the group consisting of p-chloro acetophenone, p-bromo acetophenone, p-fluoro acetophenone, p-nitro acetophenone, p-hydroxy acetophenone, p-methyl acetophenone, p-methoxy acetophenone, p-hydroxy acetophenone, 1-(2-naphthyl)-1-ethanone, 1-(6-methyl-2-naphthyl)-1-ethanone and 1-(2-furyl)-1-ethanone is used.

5. The process as claimed in claim 3, wherein a cyclic ketone selected from a group consisting of 1-tetralone, 2-tetralone, 6-methoxy-1-tetralone and 1-indalone is used.

6. The process as claimed in claim 3, wherein a β-ketoester selected from a group consisting of ethylacetoacetate, ethyl-4-chloro-3-oxobutanoate, ethyl-4-bromo-3-oxobutanoate, ethyl-4-azido-3-oxobutanoate, ethyl-3-oxo-3-phenylpropanoate, ethyl-4,4,4-trichloro-3-oxobutanoate, 4,4,4-trifluoro-3-oxobutanoate, ethyl-3-oxo-4-phenylsulfonylbutanoate, ethyl-2-oxo-1-cyclopentanecarboxylate and ethyl-2-oxo-1-cyclohexanecarboxylate is used.

7. The process as claimed in claim 3, wherein an azidoketone selected from a group consisting of 2-azido-1-phenyl-1-ethanone, 2-azido-1-(4-chlorophenyl)-1-ethanone, 2-azido-1-(4-methylphenyl)-1-ethanone, 2-azido-1-(4-methoxlphenyl)-1-ethanone, 2-azido-1-(4-fluorophenyl)-1-ethanone, 2-azido-1-(4-fluorophenyl)-1-ethanone, 2-azido-(4-tertbutyldimethyl-silyloxyphenyl)-1-ethanone, 2-azido-1-(2-furyl)-1-ethanone, 2-azido-1-(2-thienyl)-1-ethanone and 2-azido-1-(2-napthyl)-1-ethanone is used.

8. The process as claimed in claim 3, wherein a straight chain aliphatic ketone selected from a group consisting of 2-butanone, 2-pentanone, 2-hexanone, 4-methyl-2-pentanone, 3,3-dimethyl-2-butanone and 2-heptanone is used.

9. The process as claimed in claim 1, wherein the buffer used is an aqueous solution selected from the group consisting of sodium phosphate, sodium acetate, potassium phosphate, potassium acetate and tris HCl.

10. The process as claimed in claim 1, wherein the incubation period ranges from 30 to 100 hrs.

11. The process as claimed in claim 1, wherein after completion of the reaction the reductase enzyme is filtered, washed with a buffer solution and reused for carrying out reduction reaction.

12. The process as claimed in claim 1, wherein the percentage yield of optically active chiral alcohol obtained is in the range of 30–95 weight percent of ketone used.

* * * * *